United States Patent [19]

Moore et al.

[11] 4,251,518

[45] Feb. 17, 1981

[54] METHOD OF PREPARING READILY DISINTEGRABLE PHARMACEUTICAL COMPOSITIONS

[75] Inventors: Wayne R. Moore, Webster Groves; Debra K. Mann, Arnold, both of Mo.

[73] Assignee: Ralston Purina Company, St. Louis, Mo.

[21] Appl. No.: 54,498

[22] Filed: Jul. 3, 1979

[51] Int. Cl.³ .................. A61K 31/70; A61K 47/00
[52] U.S. Cl. .................................. 424/180; 424/361; 536/1
[58] Field of Search ............... 424/180, 25, 26, 35, 424/361

[56] References Cited

U.S. PATENT DOCUMENTS

| | | | |
|---|---|---|---|
| 3,034,911 | 5/1962 | McKee et al. | 424/361 |
| 3,882,228 | 5/1975 | Boncey et al. | 424/35 |
| 3,962,416 | 6/1976 | Katzen | 424/35 |
| 4,119,435 | 10/1978 | Nakao et al. | 536/1 |
| 4,167,558 | 9/1979 | Sheth et al. | 424/35 |

OTHER PUBLICATIONS

Nakao, Y., et al., Chemical Abstracts, vol. 87, 1977, 100864z.

*Primary Examiner*—Johnnie R. Brown
*Assistant Examiner*—Blondel Hazel
*Attorney, Agent, or Firm*—Virgil B. Hill; W. Dennis Drehkoff

[57] ABSTRACT

Soy polysaccharides, which are substantially high molecular weight cell wall structural components of soybean cotyledons, are mixed with a therapeutically-active substance and the mixture is made into a tablet by conventional means such as wet or dry granulation or direct compression procedures. The tablets obtained by this method have sufficient hardness and highly beneficial disintegration properties.

16 Claims, No Drawings

METHOD OF PREPARING READILY DISINTEGRABLE PHARMACEUTICAL COMPOSITIONS

BACKGROUND OF THE INVENTION

This invention generally relates to a novel method of producing readily disintegrable pharmaceutical compositions. More particularly, it relates to pharmaceutical compositions in the form of tablets containing soy polysaccharides as a disintegrant.

Pharmacological substances are commonly administered orally by means of solid dosage forms such as tablets. Tablets are solid pharmaceutical compositions containing pharmacological or therapeutically active substances in desired, accurate amounts with or without suitable diluents and prepared either by compression or molding methods. Production methods for making tablets require the presence of materials other than the therapeutically active substances for the efficient and economical manufacture of the tablet dosage form. Additional ingredients may also be present in the tablet formulation to enhance the appearance of the tablet, improve stability and aid in disintegration after administration. A disintegrating agent is a material or mixture of materials added to a tablet to facilitate its breakup or disintegration after administration. The therapeutically active substance must be released from the tablet composition as efficiently as possible to allow for its rapid dissolution. The disintegrating agent is usually admixed with the therapeutically active substance prior to granulation. Materials serving as disintegrating agents have been chemically classified as starches, clays, cellulose, algins or gums. Starches are the most widely used disintegrating agents. Other disintegrating agents include veegum HV [Gross, H. M.. and C. H. Becker. "A Comparative Study of Tablet Disintegrating Agent," *J. Amer. Pharm. Assoc. Sci. Ed.*, 41:157 (1952).]; methylcellulose, agar [Firouzabadian, A., and C. I. Huyck. 37 Some Recently Developed Chemicals as Disintegrating Agents for Compressed Tablets," *J. Amer. Pharm. Assoc. Sci. Ed.*, 43:248 (1954).]; bentonite [Granberg, C. B., and B. E. Benton. "The Use of Dried Bentonite As A Disintegrating Agent in Compressed Tablets of Thyroid," *J. Amer. Pharm. Assoc. Sci. Ed.*, 36:648 (1949).]; cellulose product [Fakouhi, T. A., et al. "Wood Products, Corncob, and Cellullose as Tablet Disintegrating Agents," *J. Pharm. Sci.*, 52:700 (1963).]; [Bequette, R. J., and C. L. Huyck. "Tablet Disintegration with Cellulose," *Drug Cosmetic Ind.*, 81:166 (1957).]; natural sponge [Crisafi, R. C. and C. H. Becker. "A study of Natural Sponge As a Disintegrating Agent in Compressed Tablets," *J. Amer. Phar. Assoc. Sci. Ed.*, 47:363 (1958)]; cation-exchange resin [Van Abbe, N. J., and J. T. Rees. "Amberlite Resin XE-88 As A Tablet Disintegrant," *J. Amer. Pharm. Assoc. Sci. Ed.* 47:487 (1958)]; alginic acid [Gerding, T. G., and Dekay, H. G. "Alginic Acid and Its Derivatives as Binding and Disintegrating Agents in Tablet Manufacture," *Drug Std.*, 23:132 (1955).]; and guar gum [Eatherton, L. E., et al. "Guar Gum As A Binder and Disintegrator for Certain Compressed Tablets," *Drug Std.*, 23:42 (1955).]

When the more common disintegrating agents, such as starch, do not provide the required functionality in a particular system, there are still other commercially available disintegrating agents such as carboxymethyl starch, polyvinylpyrolidone, sodium carboxymethyl di-cellulose, cross-linked carboxymethyl cellulose and mechanically modified starch. For various reasons, i.e., poor efficiency, deterioration, adverse effects upon the therapeutically active substance, high cost, etc., there is a need for a low cost, efficient, disintegrating agent that is effective at low use levels.

The present invention represents an improvement in the art of preparing readily disintegrable pharmaceutical compositions. A small amount of soybean polysaccharides can be mixed with the therapeutically active substance and made into a tablet by conventional tableting techniques to produce a sufficiently hard, readily disintegrable tablet.

SUMMARY OF THE INVENTION

The present invention comprises a method of preparing a readily disintegrable pharmaceutical composition by mixing a disintegratingly effective amount of heterogeneous soy polysaccharides with a therapeutically active substance and shaping said mixture into the desired tablet form by conventional tableting techniques such as dry or wet granulation or direct compression procedures. The heterogeneous soy polysaccharides are substantially components of soybean cotyledons generally obtained by treating dehulled, defatted and desolventized soy meal, flakes, or flour with an aqueous alkaline solution to solubilize and substantially remove aqueous alkaline soluble substances from the meal, flakes, or flour, separating the extracted meal, flakes, or flour and drying the extracted product.

It is an object of the present invention to produce readily disintegrable pharmaceutical compositions. And yet, another object of the present invention is to provide a pharmaceutical tablet having an efficient, stable, economical and compatible disintegrating agent. It is a further object of the present invention to utilize soy polysaccharides as a disintegrating agent in pharmaceutical compositions. An object of the present invention is to provide a method of causing a pharmaceutical composition to disintegrate upon being administered to an animal, which comprises administering to the animal a composition prepared from a mixture comprising a therapeutically active substance and a disintegratingly effective amount of soy polysaccharides.

DETAILED DESCRIPTION OF THE PREFERRED EMBODIMENTS

Pharmaceutical compositions exhibit unexpectedly good disintegrability when heterogeneous soy polysaccharides are utilized therein as a disintegrating agent. Soy polysaccharides are a group of high molecular weight carbohydrate polymers obtained by treating soybean flakes, meal or flour to remove soluble proteins and carbohydrates. The heterogeneous polysaccharides are principally cell wall structural components of the soybean cotyledons. Soy polysaccharides are easily obtained from conventional protein isolate processing and can be readily characterized as the aqueous alkaline insoluble residue from soy isolate processing.

Briefly, polysaccharides are removed from soybeans in a residue form which is obtained after the separation of a liquid proteinaceous fraction from soybean material, essentially flakes, meal or flour. These components are obtained by conventional means from the primarily carbohydrate portion of the soybean, the cell wall structural portions of the cotyledons. The flakes, meal or flour are further washed with an aqueous alkaline solution and then subjected to separation to recover the solid residue. The starting material for producing a soy polysaccharides is typically a defatted and desolventized meal, flour or flakes prepared from soybeans. Defatting or removal of the oil fraction from the soybeans is carried out by conventional methods by the use of hexane or other similar hydrocarbon solvents. The solvent extracted product is then desolventized in a conventional manner that is known to the art. The resulting dehulled, defatted and desolventized soy meal, flakes or flour are then treated with an aqueous or aqueous alkaline agent in order to effect solubilization and removal of the bulk of the soluble proteins and carbohydrates or other aqueous alkaline soluble substances from the defatted material. The material is then separated, ground and reslurried with an aqueous alkaline solution and separated. If soy flour is the starting material, grinding at this point in the procedure is not necessary. The step of removing soluble protein and carbohydrates may be repeated numerous times for obtaining an aqueous soluble residue. The resulting residue may then be cooked and dried using techniques known in the art to yield the soy polysaccharides which are utilized in the present invention. Preferably, about 40% of the soy polysaccharides should have a particle size smaller than 37 microns. This parameter is not intended to be limiting but it allows uniform mixing of the soy polysaccharides within the formulation. The soy polysaccharides swell and disperse when hydrated and uniform mixing is required for a fully disintegratable formulation. The aforementioned description of a process for obtaining soy polysaccharides is not intended to be limiting for there are many conventional processes known to those skilled in the art for the separation of the aqueous alkaline insoluble components, or the formation of soy polysaccharides from soy flour, flakes, meal or cell wall structural components of soybean cotyledons, including the processes shown in U.S. Pat. No. 4,119,435.

The soy polysaccharides exhibit a very low water solubility but are readily dispersible in water. Less than 5% of soy polysaccharide particles are soluble in cold water. The soy polysaccharides are a non-gelling material for they form a paste when mixed with water but not a continuous gel. These properties tend to make the material suitable as a disintegrating agent for pharmaceutical compositions. The Brookfield viscosity of the soy polysaccharides at a 3% solids level and at 25° C. ranges from about 20 cps to about 45 cps. The typical analysis of the soy polysaccharides is as follows:

TABLE A

|  | Percent |
| --- | --- |
| Moisture | 6.5 |
| Total Carbohydrate | 80 |
| Protein | 12 |
| Ash | 5 |
| Fat | 1.5 |

The highly fibrous polysaccharide material is termed heterogeneous for it comprises many high molecular weight carbohydrate polymers primarily composed of arabinose, galactose, glucose, mannose and xylose. The term soy polysaccharides refers to the high molecular weight carbohydrate polymers containing a mixture of polysaccharides primarily composed of arabinose, galactose, glucose, mannose and xylose. It is defined as a collective term to describe the high molecular weight fibrous carbohydrate material obtained from cell wall structural components of soybean cotyledons, including soy flakes, flour or meal. Upon analysis, the principal components of insoluble soy polysaccharides generally comprises the following in percent by weight:

TABLE B

| Arabinose | 11.9 |
| --- | --- |
| Galactose | 41.3 |
| Glucose & Mannose | 31.6 |
| Xylose | 3.1 |

Soy polysaccharides have been found to be useful as an excipient in solid dosage pharmaceutical applications. Its unique functional characteristics offer excellent disintegrating properties in direct compression and pre-granulated systems. When compared to other disintegrating agents, soy polysaccharides yield faster disintegration times when compressed at various pressures. With no intention to be unduly limitative, the amount of soy polysaccharides necessary to function as a disintegration agent depends largely on the therapeutically active substance and other diluents, fillers, binders, etc. present in the formulation. Generally, one skilled in the art would be able to surmise an effective amount of the heterogeneous soy polysaccharides needed to disintegrate various pharmaceutical compositions containing therapeutically active substances depending on the size of the granules and the desired disintegrability. Low levels of soy polysaccharides are utilized to produce tablets containing aspirin that have sufficient hardness and superior disintegration times whereas higher levels of soy polysaccharides are required to disintegrate tablets containing acetaminophen. A preferred range for the amount of soy polysaccharides that can be present in a pharmaceutical composition to produce disintegration should be from about 0.50 to about 15% by weight of the tablet. More preferably, the amount should be from about 1 to about 6% by weight. Too small an amount of the disintegrating agent results in an insufficient disintegrability of the resultant tablets and too large an amount of the disintegrating agent cannot produce tablets with a satisfactory mechanical strength due to the lacking of a binding force.

It is optional in the method of the present invention to add in combination with the disintegrating agent, small amounts of various kinds of additives including corn starch, microcrystalline cellulose, alginic acid, modified starch, etc., to aid in the disintegration of the tablet formulations with or without any binder, lubricant or filler material known to those skilled in the art.

The soy polysaccharides may be mixed with therapeutically active substance with or without other tableting ingredients in direct compression and pre-granulated systems. The method of tableting is not limiting and any type of tablet machine can be used including a single punch tablet machine and a rotary tablet machine.

The term pharmaceutical compisition is meant to be defined as any composition conaining at least a therapeutically active substance that is to be administered to an animal, including man. Preferably, the pharmaceutical composition can be defined as a compressed tablet.

A more complete understanding of the invention can be obtained by referring to the following illustrative examples which are not intended, however to be unduly limitative of the invention.

EXAMPLE I

The functionality of soy polysaccharides as a disintegrant in compressed tablets was compared to other commercially available disintegrants. Monsanto WZ grade aspirin (a combination of 20 and 40 mesh aspirin) was used as the therapeutically active substance and was compressed into tablets on a Carver press. The tablet weight was 500 mg. Selected levels of soy polysaccharides, USP corn starch, Polyplasdone XL brand of polyvinylpyrolidone and Explotab brand of carboxymethyl starch were used as disintegrating agents. Ten grams of each formulation were blended for 5 minutes in a four ounce container. Six tablets from each formulation were made using a ½ inch flat face punch at a pressure of 5000 psi for 30 seconds dwell time. Within 15 seconds of manufacture, tablets were evaluated for hardness and disintegration as described. The hardness of each tablet was evaluated by a Strong-Cobb Hardness Tester. The disintegration time was determined in accordance with the method described in the United States Pharmacopeia, 18th revision, "Disintegration Test for Uncoated Tablets". These tests were used in all the examples.

TABLE I

Composition and Properties of Aspirin Tablets Containing Selected Excipients

| Excipient | Excipient Level (%) | Aspirin (%) | Hardness (Kg/in$^2$) | Disintegration (sec.) |
|---|---|---|---|---|
| Soy Polysaccharides | | | | |
| | 0.50 | 99.5 | 10.7 | 78.4 |
| | 0.75 | 99.25 | 10.4 | 26.5 |
| | 1.0 | 99.0 | 9.5 | 16.1 |
| | 1.25 | 98.75 | 10.0 | 16.7 |
| | 1.5 | 98.5 | 10.3 | 19.0 |
| | 2.0 | 98.0 | 9.9 | 20.6 |
| | 3.0 | 97.0 | 9.0 | 31.7 |
| | 4.0 | 96.0 | 8.8 | 44.6 |
| Polyplasdone XL | 0.75 | 99.25 | 10.7 | 26.8 |
| | 1.0 | 99.0 | 11.0 | 22.7 |
| | 1.5 | 98.5 | 10.6 | 13.8 |
| | 3.0 | 97.0 | 12.3 | 7.7 |
| | 5.0 | 95.0 | 12.1 | 7.5 |
| U.S.P. Corn Starch | 2.0 | 98.0 | 9.6 | >600 |
| | 3.0 | 97.0 | 10.1 | 70.3 |
| | 4.0 | 96.0 | 11.2 | 20.6 |
| | 8.0 | 92.0 | 10.0 | 8.6 |
| | 10.0 | 90.0 | 8.4 | 5.9 |
| Explotab | 1.0 | 99.0 | 9.4 | 60.1 |
| | 2.0 | 98.0 | 10.6 | 28.4 |
| | 4.0 | 96.0 | 10.8 | 15.2 |
| | 6.0 | 94.0 | 9.6 | 17.4 |

$^a$Mean values for triplicate samples are recorded.

Soy polysaccharides show the most effective disintegration level at about 1% by weight. At levels greater or less than 1%, disintegration time increase rapidly. As concentration increased, the other excipients evaluated exhibited rapid decreases in disintegration time initially, but then leveled off. A hardness value of 7.5 kg/in$^2$ is acceptable.

EXAMPLE II

Tablet formulations were prepared using Monsanto 20 mesh crystalline aspirin and a single usage level, 1% by weight, of USP corn starch, Polyplasdone XL brand of polyvinylpyrolidone Explotab brand of carboxylmethyl starch, Sta-RX 1500 brand of mchanically modified starch, and soy polysaccharides. Each formulation was mixed for 15 minutes in a V blender. The tablets were then pressed on a Stokes 551 rotary press at 2500 tablets per minute at pressures of 1, 2, 3 and 4 tons. Tablet weight was 500 mg and a standard 13/32 inch concave face punch was utilized. Hardness of the tablets was evaluated within 2 hours, while disintegration was evaluated at approximately 24 hours. Table 2 shows the results of this experiment.

TABLE II

Properties of Aspirin Tablets with Selected Excipients at 1% Level

| Excipient | Compaction Pressure (Tons) | Hardness (SC Units) | Disintegration (sec.) |
|---|---|---|---|
| U.S.P. Corn Starch | 1 | 4.5 ± 1.0 | >600 |
| | 2 | 9.5 ± 1.8 | >600 |
| | 3 | 11.8 ± 1.8 | >600 |
| | 4 | 12.3 ± 1.0 | >600 |
| Soy Polysaccharides | 1 | 1.4 ± 0.7 | 11.0 ± 0.5 |
| | 2 | 6.8 ± 1.0 | 25.6 ± 1.7 |
| | 3 | 9.7 ± 1.0 | 33.1 ± 3.4 |
| | 4 | 9.6 ± 1.6 | 42.5 ± 5.6 |
| Polyplasdone XL | 1 | 2.3 ± 0.8 | 14.0 ± 1.2 |
| | 2 | 8.7 ± 1.0 | 38.8 ± 6.5 |
| | 3 | 9.7 ± 1.2 | 56.3 ± 7.4 |
| | 4 | 9.8 ± 1.2 | 61.4 ± 7.0 |
| Explotab | 1 | 3.2 ± 1.0 | 20.5 ± 1.2 |
| | 2 | 9.9 ± 1.4 | 65.5 ± 8.4 |
| | 3 | 10.6 ± 1.3 | 154.0 ± 24.0 |
| | 4 | 11.6 ± 1.1 | 186.0 ± 37.0 |
| Sta-RX 1500 | 1 | 2.2 ± 1.1 | >600 |
| | 2 | 8.3 ± 1.2 | >600 |
| | 3 | 10.4 ± 1.3 | >600 |
| | 4 | 11.2 ± 1.6 | >600 |

As shown in the preceding table, aspirin tablets made with soy polysaccharides exhibited the most rapid disintegration while showing satisfactory hardness.

EXAMPLE III

Tablet formulations containing acetaminophen manufactured by Monssanto were prepared and evaluated for disintegration and hardness. Pre-gelatinized corn starch was used as a binding agent in an amount of 5% by weight for each formulation. Soy polysaccharides were added at levels of 1, 2, 3, 4, 5, 6, 8, 10 and 15 percent. The formulations were prepared using a wet granulation method as follows: 190 grams of acetaminophen and 10 grams of the pre-gelatinized corn starch along with the varying amounts of soy polysaccharides were dried in a mixer for 15 minutes. Deionized water in the amount of 106 milliliters was added until a doughy mass was obtained. The mixture was then passed through a pasta maker and the resulting granules were dried at room temperature, ground, and passed through a 14 mesh screen. The formulations were tableted on a Carver press at 500 lbs per square inch for 30 seconds with a ½ inch flat face punch. The resulting weight of each tablet was 500 mg. The following table shows the disintegration times and hardness within 15 minutes after manufacture.

TABLE III

Properties of Acetaminophen-5% Corn Starch Tablets Containing Selected Levels of Soy Polysaccharides

| Acetaminophen/ Starch | Soy Polysaccharides (%) | Hardness (Kg/in$^2$) | Disintegration (sec) |
|---|---|---|---|
| 99 | 1 | 8.8 | >600 |
| 98 | 2 | 8.3 | 188 |
| 97 | 3 | 8.7 | 130 |
| 96 | 4 | 8.6 | 118 |
| 95 | 5 | 9.5 | 113 |
| 94 | 6 | 8.8 | 112 |
| 92 | 8 | 8.2 | 129 |
| 90 | 10 | 10.4 | 122 |
| 85 | 15 | 10.5 | 125 |

The optimum level for soy polysaccharides in this acetaminophen formulation is about 5 to 6% by weight.

The preceding results show that pharmaceutical compositions containing soy polysaccharides have beneficial disintegration properties. The soy polysaccharides, at low levels, perform as well as or better than some widely accepted commercial disintegrating agents.

It will be appreciated that the instant specification and examples are set forth by way of illustration and not limitation, and that various modifications and changes may be made without departing from the spirit and scope of the present invention.

What is claimed is:

1. A method of preparing readily disintegrable pharmaceutical composition which comprises mixing a disintegratingly effective amount of soy polysaccharides with a therapeutically active substance and shaping said mixture into the desired form.

2. The method of claim 1 wherein the soy polysaccharides are present in the mixture in an amount sufficient to provide from about 0.50 to about 15% by weight.

3. The method of claim 2 wherein the soy polysaccharides are present in the mixture in an amount sufficient to provide from about 1 to about 6% by weight.

4. The method of claim 1 where the soy polysaccharides are the aqueous alkaline insoluble residue from soy protein processing.

5. The method of claim 4 where the soy polysaccharides are substantially high molecular weight cell wall structural components of soybean cotyledons generally obtained by treating dehulled, defatted and desolventized material selected from the group consisting of soy meal, soy flakes and soy flour with an aqueous alkaline solution to solubilize and substantially remove aqueous alkaline soluble substances from the soy material, separating the extracted material from the extract and drying the extracted product.

6. The mthod of claim 1 wherein the soy polysaccharides have a Brookfield viscosity at 3% solids level and 25° C. of about 25 cps to about 45 cps.

7. The method of claim 1 wherein about 40% of the soy polysaccharides have a particle size smaller than about 37 microns.

8. The method of claim 1 wherein the pharmaceutical composition is a compressed tablet.

9. A method of causing a pharmaceutical composition to disintegrate upon being administered to an animal, which comprises administering to the animal a pharmaceutical composition prepared from a mixture containing a therapeutically active substance and a disintegratingly effective amount of soy polysaccharides.

10. The method of claim 9 wherein the soy polysaccharides are present in the mixture in an amount sufficient to provide from about 0.50 to about 15% by weight.

11. The method of claim 9 wherein the soy polysaccharides are present in the mixture in an amount sufficient to provide from about 1 to about 6% by weight.

12. The method of claim 9 wherein the soy polysaccharides are the aqueous alkaline insoluble residue from soy protein processing.

13. The method of claim 12 where the soy polysaccharides are substantially high molecular weight cell wall structural components of soybean cotyledons generally obtained by treating dehulled, defatted and desolventized soy meal or flakes with an aqueous alkaline solution to solubilize and substantially remove aqueous alkaline soluble substances from the meal or flakes, separating the extracted meal or flakes from the extract and drying the extracted product.

14. The method of claim 9 wherein the soy polysaccharides have a Brookfield vicosity at 3% solids level and 25° C. of about 25 cps to about 45 cps.

15. The method of claim 9 wherein about 40% of the soy polysaccharides have a particle size smaller than about 37 microns.

16. The method of claim 9 wherein the pharmaceutical composition is a compressed tablet.

* * * * *